(12) United States Patent
Gyurik

(10) Patent No.: US 8,329,760 B2
(45) Date of Patent: *Dec. 11, 2012

(54) PHARMACEUTICAL COMPOSITION

(75) Inventor: Robert J. Gyurik, Exeter, NH (US)

(73) Assignee: CPEX Pharmaceuticals, Inc., Wilmington, DE (US)

( * ) Notice: Subject to any disclaimer, the term of this patent is extended or adjusted under 35 U.S.C. 154(b) by 41 days.

This patent is subject to a terminal disclaimer.

(21) Appl. No.: 12/505,421

(22) Filed: Jul. 17, 2009

(65) Prior Publication Data

US 2009/0286715 A1 Nov. 19, 2009

Related U.S. Application Data

(63) Continuation of application No. 10/481,309, filed as application No. PCT/US02/19849 on Jun. 24, 2002.

(60) Provisional application No. 60/300,293, filed on Jun. 22, 2001.

(51) Int. Cl.
  *A61K 8/02* (2006.01)

(52) U.S. Cl. .................................. 514/937; 514/947
(58) Field of Classification Search .................. 424/401; 514/937, 947

See application file for complete search history.

(56) References Cited

OTHER PUBLICATIONS

Kowarski et al. "Comparing the Biological Activity of Humulin R and Novolin R Using an Intravenous Bioassay". Pharmaceutical Research, vol. 5, No. 4, 1988.*

* cited by examiner

*Primary Examiner* — Renee Claytor
(74) *Attorney, Agent, or Firm* — Ohlandt, Greeley, Ruggiero and Perle, LLP

(57) ABSTRACT

A pharmaceutical compositions in the form of an emulsion and containing a continuous liquid phase, for example, an aqueous phase, liquid droplets dispersed in the continuous phase, a pharmaceutically active compound, a Hseih enhancer, and a hydrocolloid emulsifying agent and in which, for example, the active compound is dissolved in the aqueous phase or in the liquid droplets, and the use of such composition to treat a condition in a patient, for example, diabetes.

1 Claim, No Drawings

PHARMACEUTICAL COMPOSITION

FIELD OF THE INVENTION

The present invention relates to a composition useful for drug delivery. More particularly, the present invention relates to a pharmaceutical composition which includes an enhancer, that is, a material which is capable of increasing the rate of passage of a pharmaceutically-active compound through a body membrane.

The present invention will be described initially with respect to its use in the intra-nasal delivery of insulin. It should be understood, however, that the present invention can be used also in other applications, as exemplified in the description of the invention.

Diabetes is the fourth leading cause of death in the U.S. Type I diabetes is related to problems with the production of insulin by the body. Type II diabetes is related to problems with the use of insulin by the body and such problems may also lead to problems with the production of insulin by the body. Insulin is a hormone which functions to transport glucose from blood to the inside of cells where the glucose provides the body with a source of energy. People who suffer from diabetes often require the administration of exogenous insulin.

Various ways to treat diabetes have been developed. For example, diabetes has been treated by daily injections of insulin. This form of treatment, however, is uncomfortable and leads to problems of patient compliance. Another method of treating diabetes involves the intra-nasal administration of a composition containing insulin. This form of administration is more convenient. In addition, it has been found recently that certain agents which produce an antigenic effect when administered by injection do not produce an antigenic effect when administered intra-nasally. Intra-nasal administration thus leads to fewer immunological problems for the patient. The present invention includes within its scope the intra-nasal method of treating diabetes and other aspects of drug delivery.

Reported Developments

It is known to treat a condition in a patient by the use of a composition in the form of an intra-nasal spray which contains a pharmaceutically-active compound. For example, U.S. Pat. No. 5,989,535 discloses an intra-nasal spray which contains insulin. Such intra-nasal sprays, however, have had limited success because various pharmaceutically-active compounds, including, for example, insulin, are not particularly effective in penetrating the mucous membrane of the nasal passage.

The use of an enhancer to improve the delivery of a pharmaceutically-active compound to the target area has been proposed. For example, U.S. Pat. No. 5,023,252 to D. Hsieh, assigned to the same assignee as the present invention, discloses a biphasic system (two separate compositions) in which an intra-nasal spray of a composition containing insulin is supplemented with a spray of a composition which contains an enhancer. The biphasic system described in the '252 patent consists of a solution of enhancer which is lipophilic and a solution of insulin which is hydrophilic, the solutions being non-miscible with each other. The use of such a biphasic system is inconvenient, however.

The use of a surfactant to improve the delivery of a pharmaceutically-active compound has been proposed also. Examples of such surfactants are bile salts and phospholipids. Although systems in which surfactants are used may not require biphasic delivery, the use of a surfactant as the enhancer is disadvantageous in that such surfactants are known to irritate the mucous membrane. Indeed, there are reports that the intra-nasal delivery of effective amounts of insulin requires the use of surfactants in amounts which have an irritating effect on the mucous membrane. See, e.g., K. Drier, et al., Diabetic Medicine, 9: 335-340 (1992); and M. Hinchcliffe and L. Illum, Advanced Drug Delivery Reviews, 35: 199-234 (1999).

U.S. Pat. No. 5,118,676 to Minaskanian et al., U.S. Pat. No. 5,196,410 to Francoeur et al., and the aforementioned '252 patent disclose compositions in which surfactants are used for the purpose of aiding in the formation of a homogeneous composition comprising a lipophilic enhancer and a pharmaceutically-active compound. The amount of surfactant needed to accomplish this effectively, however, is an amount which irritates the mucous membrane.

The present invention provides an improved non-irritating means for delivering a pharmaceutically-active compound, for example, insulin, and an enhancer to treat a condition in a patient, for example, by intra-nasal application.

SUMMARY OF THE INVENTION

The present invention provides a pharmaceutical composition which is in the form of an emulsion and which comprises: (A) a liquid continuous phase; (B) liquid droplets dispersed in said continuous phase; (C) a pharmaceutically-active compound; (D) a Hsieh enhancer; and (E) a hydrocolloid emulsifying agent. In preferred form, the composition includes a continuous phase comprising an aqueous solution of the pharmaceutically-active compound, for example, insulin and liquid droplets comprising an organic solution of the enhancer.

Another aspect of the present invention is the provision a method for treating a condition in a patient comprising the step of delivering to said patient a pharmaceutical composition which is in the form of an emulsion and which comprises: (A) a continuous phase; (B) liquid droplets dispersed in said continuous phase; (C) a pharmaceutically-active compound; (D) a Hsieh enhancer; and (E) a hydrocolloid emulsifying agent. Such method can include, for example, the step of spraying the composition into the nostrils of the patient or the step of dropping or spraying into the eye or the sac of the eye of the patient the pharmaceutical composition.

Compositions within the scope of the present invention can be made in non-irritating stable and homogeneous form capable of being sprayed, aerosolized, or nebulized to provide an even distribution of the pharmaceutically-active compound and the enhancer on the body membrane of the patient. Compositions of the present invention are especially advantageous in cases where the enhancer is lipophilic and the pharmaceutically-active compound is hydrophilic or amphiphilic.

The composition of the present invention can be prepared in the form of a monophasic system which has numerous advantages relative to the prior art biphasic delivery system in which a first composition comprising the lipophilic enhancer and a second composition comprising the hydrophilic or amphiphilic pharmaceutically-active compound are administered separately. Some disadvantages of the prior art system are that a homogeneous distribution of the enhancer and the pharmaceutically-active compound is not ensured and the enhancer and the pharmaceutically-active compound do not simultaneously contact the target membrane. In contrast, the present invention provides a monophasic delivery system in which such a lipophilic enhancer and a non-lipophilic pharmaceutically-active compound may be delivered simultaneously to the membrane in a stable and homogeneous composition.

DETAILED DESCRIPTION OF THE INVENTION

The composition of the present invention comprises a pharmaceutically-active compound. Essentially any pharmaceutically-active compound, or a mixture of two or more such compounds, capable of being delivered across a body membrane may be used in the practice of the present invention. The term "pharmaceutically-active compound" includes drugs and precursors, congeners, salts, complexes, analogs, and derivatives of said drugs. The compound may be therapeutic, prophylactic, or diagnostic in nature. For the purpose of the present application, the term "membrane" is meant to include skin and mucous membrane.

Examples of pharmaceutically-active compounds which may be employed in the practice of the present invention include: compounds useful in the treatment of diabetes, for example, insulin, proinsulin, preproinsulin, and glucagon-like peptides (GLPs); calcitonin and calcitonin gene-related peptides; growth hormones; growth hormone-releasing agents; cancer-treating agents, for example, somatostatins (SRIFs) and analogs thereof; gonadotropin-releasing agents (GnRHs—also known as luteinizing hormone-releasing hormone agonists (LHRHs)); gonadotropin-releasing hormone antagonists, for example, Antide; delta-sleep-inducing peptides (DSIPs); opioids; anti-obesity agents; anti-inflammatory agents, for example, hamburger peptide and analogs thereof; angiogenin antagonists; anti-opiate peptides, for example, morphine-modulating neuropeptides; beta-antagonists, for example, albuterol; anxiolytic agents, for example, diazepam, midazolam, barbiturates, paroxetine, imipramine, and related psychotrophic compounds; beta-blockers; appetite-enhancing compounds; narcotic and opioid analgesics; sex hormones, for example, testosterone, progesterone, and estradiol; and metabolic regulating peptides, for example, parathyroid hormone (PTH), thyroid stimulating hormone, thymic humoral factor (THF), and follicle stimulating hormone (FSH).

In embodiments of the present invention in which insulin is used, the composition comprises a pharmaceutically-effective amount of insulin capable of treating insulin deficiency in a patient. Essentially any suitable form of insulin, its precursors, congeners, and the salts, complexes, analogs, and derivatives thereof may be employed. An example of a salt of insulin which may be used in the practice of the present invention is the zinc salt of insulin. Examples of derivatives of insulin which may be used in the practice of the present invention are those which include modified forms of internal or terminal amino acids, for example, lysine/proline-substituted insulin derivatives. Such derivatives may be derived synthetically. Water-soluble forms of insulin, its precursors, congeners, and the salts, complexes, analogs, and derivatives thereof may be used in the practice of the present invention. Human recombinant insulin is particularly preferred. The pH of the insulin-containing composition of the present invention is preferably above about 7 because insulin has marginal water solubility between pH 5 and pH 7.

In another embodiment of the present invention, the composition comprises a pharmaceutically-effective amount of a growth hormone or, more preferably, a growth hormone-releasing agent capable of stimulating growth in children or counteracting the deleterious effects of aging, such as, for example, muscle weakness, body fat increases, and skin fragility in adults. Essentially any suitable growth hormone or growth hormone-releasing agent may be employed. Examples of such growth hormone-releasing agents include: somatoliberins and growth hormone-releasing hormone active fragments, such as, for example, hGRF (1-29) amide and hexarelin (GHRP-6). In particularly preferred embodiments, more than one growth hormone-releasing agent may be used in combination. A preferred combination comprises growth hormone-releasing factor (GRF) and growth hormone releasing peptide (GHRP). This combination has been reported to act by separate mechanisms for the release of endogenous growth hormone.

In an additional embodiment of the present invention, the composition comprises a pharmaceutically-effective amount of a reproductive hormone peptide capable of treating prostate cancer or relieving the symptoms of fibrosis or endometriosis. Essentially any suitable reproductive hormone peptide can be used, including, for example, luteinizing hormone (LH) and its analogs, follicle-stimulating hormone (FSH) and its analogs, and gonadotropin-releasing hormone (GnRH—also known as luteinizing hormone releasing hormone (LHRH)) and its analogs, for example, goserelin, nafarelin, buserelin, and leuprolide. Examples of suitable reproductive hormone peptides are described also in K. Saeb-Parsy, et al., Instant Pharmacology, 57-62 (1999). LHRH-Lamprey III and closely related analogs thereof are particularly preferred because of their relatively high activity. Yu et al., PNAS, 94: 9499 (1997).

In still another embodiment of the present invention, the composition comprises a pharmaceutically-effective amount of an opioid peptide or peptidomimetic (synthetic peptide) capable of reducing pain. Essentially any suitable opioid peptide or peptidomimetic may be employed. Examples of suitable opioid peptides include enkephalins, endorphins, exorphins, dynorphins, endomorphins, syndyphalins, BAM peptides, metorphamide, and valorphin. Shorter peptides are preferred, with especially potent shorter peptides such as, for example, the endomorphins being particularly preferred. For use in an emulsion of the present invention, opiate alkaloids of the morphine class are preferred because the free bases of such alkaloids are capable of stabilizing emulsions formed using acidic emulsifying agents. This functions to stabilize the resulting emulsion without the need for further pH modifiers. Examples of such opiate alkaloids are morphine, codeine, oxycodone, hydrocodone, hydromorphone, fentanyl, sufentanil, levorphanol, meperidine, methadone, and the like.

Yet another embodiment of the present invention is a composition which comprises a pharmaceutically-effective amount of an anti-obesity agent which is capable of alleviating a disorder which causes obesity in mammals, particularly humans. Essentially any suitable anti-obesity agent may be employed. Examples of such agents include galanins, bombesin, incretins such as glucagon and glucagon-like peptides, insulin-like growth factors, leptins, melanotropin, peptides which interact with the melanocortin receptor, and analogs thereof. Glucagon and glucagon-like peptides are preferred, with GLP-1 being particularly preferred. Leptins are preferred also, with leptin fragments, such as leptin 22-56 (obese gene peptide), being particularly preferred. Peptides which interact with the melanocortin receptor such as, for example, alpha-MSH and their analogs, are preferred (such peptides have been reported to decrease appetite. Science, 291: 1691 (2001)).

A further embodiment of the present invention is a composition which comprises a pharmaceutically-effective amount of an appetite-enhancing compound which is capable of increasing appetite in mammals, preferably humans. Essentially any suitable appetite-enhancing compound may be employed. Examples of such appetite-enhancing compounds include compounds which serve as antagonists of the aforementioned anti-obesity agents. Science, 291: 1691 (2001).

There are species of pharmaceutically-active compounds for use in the present invention that are Bronstead-Lowry bases (for example, opiate alkaloids) whose free base is capable of modifying the pH of an acidic emulsifying agent, thus aiding in the stabilization of the resulting emulsion. When such a base is used, the use of an additional pH modifier for the purpose of aiding in the stabilization of the emulsion may not be necessary. With respect to such pharmaceutically-active compounds, a free base having a pKa greater than about 9 is preferred, with those with a pKa greater than about 9.5 being particularly preferred.

Preferred also for use as a pharmaceutically-active compound in the present invention are peptides of moderate size, preferably peptides weighing no greater than about 20 kilodaltons, most preferably not greater than about 10 kilodaltons. Such peptides may be more easily delivered through a membrane.

The pharmaceutically-active compound is present in the composition in a pharmaceutically-effective concentration. Preferably, the concentration does not exceed the maximum amount that remains soluble in the composition. For guideline purposes, it is believed most applications will involve the use of the pharmaceutically-active compound in an amount of about 0.005 to about 10 wt. % of the composition, more likely an amount of about 0.01 to about 5 wt. % of the composition, and most likely in an amount of about 0.1 to about 2 wt. % of the composition.

The composition of the present invention comprises also an enhancer capable of increasing the rate of passage of the pharmaceutically-active compound through a membrane. Essentially any suitable solid or liquid enhancer or a mixture of such enhancers may be used in the practice of the present invention. Preferred enhancers are characterized by at least one of the following properties: membrane-compatibility; lipophilic nature; low level of irritability or no irritability to the target membrane; emolliency; and being a solid at room temperature when in neat form.

Membrane-compatible permeation enhancers are particularly preferred for use in the present invention. The term "membrane-compatible permeation enhancer" means a compound which increases the rate of delivery of the pharmaceutically-active compound through the membrane without damage. Examples of lipophilic membrane-compatible enhancers for use in the present invention include: fatty acids; fatty alcohols; alkyl esters, such as isopropyl myristate and myristyl myristate; and cycloaliphatic enhancers, for example, the enhancers described in U.S. Pat. No. 5,023,252 to Hsieh (hereafter "the Hsieh enhancers"). Preferred enhancers are normally solid lipophilic enhancers. The choice of enhancer for use with a particular pharmaceutically-active compound is within the skill of the art.

Hsieh enhancers are especially preferred for use in the present invention because, in addition to being membrane-compatible and lipophilic, they exhibit no irritability to the target membrane. The Hsieh enhancers are enhancers of the formula:

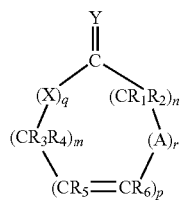

wherein X and Y are oxygen, sulfur or an imino group of the structure

or =N—R, with the proviso that when Y is an imino group, X is an imino group, and when Y is sulfur, X is sulfur or an imino group, A is a group having the structure

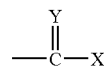

wherein X and Y are as defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$, and $R_6$ is independently hydrogen or an alkyl group having from 1 to 6 carbon atoms which may be straight chained or branched, provided that only one of $R_1$ to $R_6$ can be alkyl group, with the proviso that when p, q and r are 0 and Y is oxygen, then m+n is at least 11, and with the further proviso that when X is an imino group, q is equal to 1, Y is oxygen, and p and r are 0, then m+n is at least 11.

Especially preferred Hsieh enhancers for use in the present invention are macrocyclic enhancers. The term "macrocyclic" is used herein to refer to cyclic compounds having at least 12 carbons in the ring. Examples of preferred macrocyclic enhancers which may be used in the present invention include: macrocyclic ketones, for example, 3-methylcyclopentadecanone (muscone), 9-cycloheptadecen-1-one (civetone), and cyclopentadecanone (normuscone); and cyclic esters, for example, pentadecalactones such as oxacyclohexadecan-2-one (cyclopentadecanolide; ω-pentadecalactone).

Oxacyclohexadecan-2-one is particularly preferred since it has been shown to exhibit a surprising lack of irritation to the skin, mucous membranes, and the eye. The use of 100% oxacyclohexadecan-2-one in a rabbit eye does not produce irritation. Occluded patch studies in rabbit and guinea pig at high concentrations have shown a lack of irritation also. In addition, intra-nasal studies in rats involving the use daily for 24 days of a 2% oxacyclohexadecan-2-one formulation containing also insulin have shown a complete absence of untoward effects both locally and systemically.

The enhancer is present in the composition in a concentration effective to enhance penetration through the membrane of the pharmaceutically-active compound to be delivered. Various considerations should be taken into account in determining the amount of enhancer to use. Such considerations include, for example, the amount of flux (rate of passage through the membrane) achieved and the stability and compatibility of the components in the formulations. For guideline purposes, it is believed most applications will involve the use of the enhancer in an amount of about 0.05 to about 10 wt. % of the composition, more likely in an amount of about 0.1 to about 5 wt. % of the composition, and most likely in an amount of about 1.0 to about 3 wt. % of the composition.

The composition of the present invention comprises also an emulsifying agent for use in aiding the formation of an emulsion. Essentially any suitable hydrocolloid emulsifying agent, typically a solid material, or a mixture of two or more such emulsifying agents can be used in the practice of the present invention. Hydrocolloid emulsifying agents include: vegetable derivatives, for example, acacia, tragacanth, agar, pectin, and carrageenan; animal derivatives, for example, gelatin, lanolin, cholesterol, and lecithin; semi-synthetic agents, for example, methylcellulose and carboxymethylcellulose; and synthetic agents, for example, acrylic emulsifying agents such as carbomers. The hydrocolloid emulsifying agent forms hydrocolloids (hydrated lyophilic colloids) around the emulsified liquid droplets of the emulsion. The hydrocolloid serves as a protective layer around each emulsified droplet which physically repulses other droplets, thus hindering Ostwald ripening (the tendency of emulsified droplets to aggregate). In contrast, other emulsifying agents typically protect the emulsified droplets by forming a liquid crystalline layer around the emulsified droplets. In compositions which employ a liquid crystalline layer-forming emulsifying agent, the hydrophilic-lipophilic balance (HLB) of the oil phase of the emulsion must be matched with that of the emulsifying agent to form a stable emulsion and, often, one or more additional emulsifying agents (secondary emulsifying agents) must be added to further stabilize the emulsion. The aforementioned liquid crystalline layer also retards the release of the compounds of the dispersed phase upon contact with the target substrate.

The hydrocolloid emulsifying agents for use in the composition of the present invention include compounds which exhibit a low level of irritability or no irritability to the target membrane and which have good bioadhesive and mucoadhesive properties. Examples of hydrocolloid emulsifying agents which exhibit such properties include cellulosic emulsifying agents and acrylic emulsifying agents, including, for example, those which have an alkyl group containing from about 10 to about 50 carbon atoms. Particularly preferred acrylic emulsifying agents for use in the present invention are copolymers of a carboxylic acid and an acrylic ester (described, for example, in U.S. Pat. No. 3,915,921 to Schlatzer and U.S. Pat. No. 4,509,949 to Huang et al.), with those which are cross-linked being especially preferred. An example of such an especially preferred emulsifying agent for use in forming an oil-in-water emulsion is "acrylates/$C_{10-30}$ alkyl acrylate crosspolymer", a cross-linked polymer of acrylic acid and ($C_{10-30}$) alkyl acrylates. Acrylates/$C_{10-30}$ alkyl acrylate crosspolymer is available from Noveon, Inc. (previously B.F. Goodrich) and is sold under the trade name Pemulen®. Acrylates/$C_{10-30}$ alkyl acrylate crosspolymer has a small lipophilic portion and a large hydrophilic portion, thus allowing for it to function as a primary emulsifier for the formation of oil-in-water emulsions. In addition, acrylates/$C_{10-30}$ alkyl acrylate crosspolymer is capable of releasing the compounds of the dispersed phase upon contact with a substrate, namely, biological membranes or mucosa and will not re-wet (the oil phase will not re-emulsify upon contact with water). Additional information regarding acrylates/$C_{10-30}$ alkyl acrylate crosspolymer, which is listed in the U.S. Pharmacopeia, is provided in Noveon publications TDS-114, 117, 118, 124, 232-3, and 237, and PDS Pemulen 1622.

In forming an emulsion in which the water-insoluble enhancer is a normally solid material, the enhancer is dissolved in a suitable solvent. If the enhancer is a normally liquid material which is water-immiscible, a suitable solvent for the enhancer may or may not be used, as appropriate.

The emulsifying agent is present in the composition in a concentration that is effective to form the desired liquid emulsion. For guideline purposes, it is believed most applications will involve the use of the emulsifying agent in an amount of about 0.001 to about 5 wt. % of the composition, more likely about 0.01 to about 5 wt. % of the composition, and most likely about 0.1 to about 2 wt. % of the composition.

The composition of the present invention may exist in various forms, for example, an oil-in-water emulsion, a water-in-oil emulsion, and a water-in-oil-in-water emulsion. The active compounds of the compositions of the present invention may exist in either the continuous or the dispersed phase or in both phases depending upon whether the compounds are hydrophilic, lipophilic, or amphiphilic. In an example of a preferred embodiment of the present invention, the emulsion comprises oil droplets dispersed in a continuous aqueous phase with a lipophilic enhancer being contained in the oil droplets and a water-soluble pharmaceutically-active compound dissolved in the continuous aqueous phase.

The composition of the present invention may include, as an optional ingredient, particulate solids dispersed in the composition. For example, the composition may include an additional pharmaceutically-active compound dispersed in the liquid continuous phase of the emulsion in the form of microcrystalline solids or nanoparticulates.

While the hydrocolloid emulsifying agent forms a protective layer around the emulsified liquid droplets, thus forming a stable emulsion by hindering Ostwald-ripening without the need for further stabilizing agents, in some instances it may be desirable to further improve the stability of the emulsion. Such may be accomplished by the addition of Ostwald-ripening inhibitors and/or surfactants.

An Ostwald-ripening inhibitor is a material which reduces the tendency of emulsified droplets to aggregate and form larger droplets. Essentially any suitable Ostwald-ripening inhibitor or a mixture of such inhibitors may be used to improve further the physical stability of the emulsion. Preferred Ostwald-ripening inhibitors are hydrophobic agents such as hydrocarbons and hydrocarbon waxes. Examples of hydrophobic agents are petrolatum, hexadecane, and long-chain esters, for example, octyl palmitate. The Ostwald-ripening inhibitor is present in the composition in a concentration effective to prevent the emulsified droplets, particularly relatively small droplets (for example, one micron in diameter), from aggregating into larger droplets which may result in settling (materials settling to the bottom) or creaming (oils rising to the top). For guideline purposes, it is believed most applications will involve the use of the Ostwald-ripening inhibitor in an amount of about 0.001 to about 5 wt. % of the composition and more likely in an amount of about 0.1 to about 1 wt. % of the composition.

Surfactants may be used to reducing the size of the emulsified droplets to a size smaller than that produced by the use of the emulsifying agent. Essentially any suitable surfactant or mixture of surfactants can be used in the practice of the present invention, including, for example, anionic, cationic, and non-ionic surfactants. Preferred surfactants are non-ionic surfactants, with those having a hydrophilic-lipophilic balance (HLB) of from about 7 to about 14 being particularly preferred. Examples of such non-ionic surfactants are PEG-60 corn glycerides, PEG-20 sorbitan monostearate, phenoxy-poly(ethyleneoxy)ethanol, sorbitan monooleate, and the like. Especially preferred are compendial surfactants such as those described in compendia such as the Food Chemicals Codex, National Formulary, U.S. Pharmacopeia, and the Code of Federal Regulations. It is preferred that the average diameter of the droplets of the emulsion be from about 500 mn to about 20 μm and more preferably from about 1 μm to about 10 μm. For guideline purposes, it is believed most applications will involve the use of the surfactant in an amount of no greater than about 2 wt. % of the composition and more likely no greater than about 0.5 wt. % of the composition.

The composition of the present invention may comprise also a solvent capable of solvating at least one of the compounds of the composition of the present invention. Essentially any such solvent or mixture of solvents may be used in the practice of the present invention. Solvents for use in the present invention include water and non-aqueous solvents. Examples of non-aqueous solvents include propylene glycol, polypropylene glycol, polyethylene glycol, cottonseed oil, petrolatum, and Vitamin E acetate. The solvents are preferably compendial solvents, for example, those listed in the National Formulary or the U.S. Pharmacopeia. Especially preferred solvents are those which perform an additional function in the composition, for example, functioning also as an emollient, a humectant, a protein stabilizer, an Ostwald ripening inhibitor, and/or a crystallization inhibitor. Examples of such solvents include: glycerin; polyethylene, polypropylene; silicones, such as dimethylpolysiloxane; cottonseed oil; petrolatum; and Vitamin E acetate.

The solvent is present in the composition in a concentration sufficient to solubilize the particular compound to be dissolved, for example, a solid pharmaceutically-active compound, an enhancer, and/or other ingredient. For guideline purposes, it is believed most applications will involve the use of a non-aqueous solvent (apart from water) in an amount of about 0.1 to about 10 wt. % of the composition, more likely about 0.5 to about 8 wt. % of the composition, and most likely of about 1.0 to about 5 wt. % of the composition. Water is present typically as a major substituent and may be present in concentrations, for example, as high as about 99 wt. % of the composition.

The composition of the present invention may comprise also a crystallization inhibitor capable of inhibiting the crystallization of the compounds of the composition of the present invention. Essentially any suitable crystallization inhibitor or mixture of such inhibitors can be used in the practice of the present invention. Crystallization, if allowed to proceed, renders the emulsion unstable and has an adverse effect on shelf life. Preferred crystallization inhibitors function by lowering the temperature at which the involved compound crystallizes. Examples of such crystallization inhibitors include natural oils, oily substances, waxes, esters, and hydrocarbons. Examples of natural oils or oily substances include Vitamin E acetate, octyl palmitate, sesame oil, soybean oil, safflower oil, avocado oil, palm oil, and cottonseed oil. It should be appreciated from the above description of solvents that can be used in formulating compositions of the present invention that there are compounds which function both as a solvent and a crystallization inhibitor.

Inhibitors which are capable of lowering the temperature of crystallization of the involved compound to below about 25° C. are particularly preferred, with those capable of lowering the crystallization of the involved compound to below about 5° C. being especially preferred. Examples of especially preferred crystallization inhibitors for use in inhibiting the crystallization of oxacyclohexadecan-2-one include hexadecane, isopropyl myristate, octyl palmitate, cottonseed oil, safflower oil, and Vitamin E acetate.

The crystallization inhibitor is present in the composition in a concentration effective to inhibit the crystallization of a compound of interest. For guideline purposes, it is believed most applications will involve the use of the crystallization inhibitor in an amount of about 0.001 to about 5 wt. % of the composition, more likely about 0.01 to about 2 wt. % of the composition, and most likely about 0.1 to about 1 wt. % of the composition.

Still another optional ingredient of the composition of the present invention is a preservative capable of preventing oxidation, microbial growth, or contamination. Essentially any suitable preservative or mixture of preservatives may be used in the practice of the present invention. Preferred preservatives are: food additive anti-microbial agents, for example, quaternary ammonium salts, sorbic acid, acetic acid, and benzoic acid or salts thereof; and antioxidants, for example, Vitamin C, Vitamin E, butylated hydroxyanisole (BHA), and butylated hydroxytoluene (BHT). Examples of preferred antimicrobial preservatives are benzalkonium chloride and cetyl pyridinium chloride.

The preservative is present in the composition in a concentration effective to inhibit microbial growth, the oxidation of the components of the composition, or contamination of the composition. For guideline purposes, it is believed most applications will involve the use of the preservative in an amount of about 0.0001 to about 1.0 wt. % of the composition and more likely in an amount of about 0.005 to about 0.1 wt. % of the composition.

In embodiments of the present invention which comprise a peptide or a protein, the composition may comprise also an enzyme inhibitor which is capable of preventing the breakdown of a peptide or protein, for example, at the site of absorption. Essentially any suitable enzyme inhibitor or mixture of enzyme inhibitors may be used in the practice of the present invention. Preferred enzyme inhibitors are leupeptin, bestatin, and aprotinin, as described in Bi, M. and J. Singh, Pharmaceutical Development and Technology, 5: 417-22 (2000). Depending on the enzymatic cleavage site in any given peptide or protein, different enzyme inhibitors may be used. For example, in embodiments of the present invention which comprise LHRH, bestatin is preferred.

The enzyme inhibitor can be used in a concentration effective to inhibit enzymatic degradation at the site of administration. For guideline purposes, it is believed most applications will involve the use of the enzyme inhibitor in an amount of about 0.0001 to about 1.0 wt. % of the composition and more likely about 0.005 to about 0.1 wt. % of the composition.

The viscosity of the liquid emulsion of the present invention can vary over a wide range, for example, between about 100 and 60,000 cp. Viscosity is measured using an Instron viscometer at a temperature of 25° C. Speaking generally, the higher the viscosity, the more stable the emulsion, the better the non-drip properties, and the better the sustained-release properties. One of the important factors that is determinative in selecting the viscosity value of the composition is the means by which the composition is applied to the body membrane. For example, it is believed that the composition will be used widely by spraying the composition into the nostrils of the patient by use, for example, of a hand-held pump, including, for example, a precompression pump. For such applications, it is recommended that the viscosity of the composition be about 500 to about 20,000 cp, preferably about 1,000 to about 10,000 cp. For applications in which the emulsion is used in the form of a lotion or cream, it is recommended that the viscosity of the composition be about 5,000 to about 60,000, preferably about 10,000 to about 30,000 cp. For the purpose of increasing the viscosity of a composition, a thickening agent can be used. Essentially any suitable thickening agent can be used in the practice of the present invention. Preferred thickening agents are acrylic and cellulosic thickeners, for example, carbomers, hydroxyethyl-celluloses, and hydroxypropylmethyl-celluloses. The thickening agent can be used in a concentration effective to increase the viscosity of the composition to the desired extent, for example, about 0.1 to about 5 wt. %, preferably about 0.25 to about 3 wt. %.

The pH of the composition may have an effect on various compounds which comprise the composition, for example, on the activity or solubility of the compound. For example, the pH of the composition may have an effect on the ability of an emulsifying agent to impart to the composition desired stability properties or on the ability of a thickening agent to impart to the composition a desired viscosity. The desired pH of the composition may be controlled or adjusted by including in the composition a pH modifier. Essentially any suitable pH modifier or mixture of pH modifiers may be used in the practice of the present invention. For use in optimizing the stability of an emulsion formed using acrylates/$C_{10-30}$ alkyl acrylate crosspolymer, preferred pH modifiers have a pKa greater than about 9, with a pKa greater than about 9.5 being particularly preferred and/or are compendial and approved for use by governmental agencies in food and pharmaceutical formulations. Examples of pH modifiers which exhibit both of the above properties include triethanolamine, TRIS amino, triethylamine, triethanolamine, 2-amino-2-methyl-1-propanol, sodium hydroxide, ammonium hydroxide, and potassium hydroxide.

The pH modifier is present in the composition in a concentration effective to impart to the composition the desired pH. For guideline purposes, it is believed most applications will involve the use of the pH modifier in an amount of about 0.01 to about 5 wt. % of the composition and more likely about 0.1 to about 2 wt. % of the composition.

The composition of the present invention may include also other optional ingredients which are art-recognized and in art-recognized quantities. For example, materials may be added to modify the rheology, feel, slip, humectancy, and other desirable physical properties that a practitioner may deem desirable.

The composition of the present invention may be applied in pharmaceutically effective amounts by various routes of administration, including, for example, subcutaneously, transdermally, vaginally, bucally, ophthalmically, and intra-nasally. Ophthalmic and intra-nasal administration are preferred. Periodic application may be required to maintain the desired drug dosage regimen.

If intra-nasal application is desired, the composition may be placed in an intra-nasal spray-dosing device or atomizer and applied by spraying into the nostrils of a patient for delivery to the mucous membrane of the nostrils. If ophthalmic application is desired, the composition may be placed in an ocular droplet device and applied by spraying into the eye or the sac of the eye of a patient. A sufficient amount is applied to achieve the desired systemic or localized drug levels. For an intra-nasal spray, up to about 200 microliters is typically applied, with an application of about 50 to about 150 microliters being preferred. One or more nostrils may be dosed and application may occur as often as desired or as often as is necessary.

The composition of the present invention may be formulated by the use of conventional means, for example, by mixing, stirring, folding, slurrying, and sonicating the ingredients. Conventional equipment may be used. One of the advantages of the present invention is the ability to formulate the composition without resorting to unusual means to achieve the desired result. It has been observed that various embodiments of the composition can be made without having to use high-energy mixing or sonication to achieve relatively small and homogeneous droplets. Simple glassware or stainless steel mixing vessels may be used. The composition can be formulated typically at room temperature or slightly above (below about 60° C.) and at atmospheric pressures.

EXAMPLES

Examples below are illustrative of compositions of the present invention. The concentrations of the ingredients comprising the compositions are given in percent by weight relative to the total weight of the composition.

Example Nos. 1 to 5 are examples of compositions of the present invention for use in an intra-nasal spray.

In Example Nos. 1 to 3, the ingredients of Part A were mixed by mechanically stirring at 40° C. until homogeneous. The ingredients of Part B were mixed separately using magnetic stirring at 40° C. until homogeneous and then added to Part A. The resulting mixture was stirred vigorously and Part C was added slowly to the mixture. Following the addition of Part C, Part D was added and the resulting mixture was stirred for 4 hours at 40° C. The mixture was allowed to cool to room temperature while stirring for an additional 18 hours. Part E was then added while shaking and stirring for 4 hours. The resulting mixture is referred to as the "Premix".

A solution of pharmaceutically-active compound in the concentration desired was prepared separately. The pharmaceutically-active compound was mixed with and dissolved in water by agitating until homogeneous. A pH modifier was then added and the resulting mixture was mixed by rolling on a roller mill at 120 rpm at room temperature until the solution was homogeneous.

The Premix was added to the aqueous solution of pharmaceutically-active compound at room temperature and the resulting mixture was mixed by rolling on a roller mill at 120 rpm until the final mixture composition was homogeneous.

Example No. 1

This Example describes the preparation of a composition which can be used as an intra-nasal spray for the delivery of human recombinant insulin.

Premix

|  | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.67% |
| petrolatum - Protopet (Witco) - solvent, Ostwald-ripening inhibitor | 0.14% |
| Part B | |
| propylene glycol, USP - solvent | 1.00% |
| glycerin, USP - cosolvent, emollient, humectant and protein stabilizer | 2.00% |
| water, sterile and deionized | 44.05% |
| Part C | |
| acrylates/$C_{10-30}$ alkyl acrylate crosspolymer - Pemulen-TR2, NF grade (Noveon, Inc.) - emulsifier and thickener | 0.10% |
| Part D | |
| benzalkonium chloride, 50% aqueous solution - Maquat (Mason) - preservative | 0.01% |
| Part E | |
| triethanolamine, NF - pH modifier | 0.03% |

Solution of Pharmaceutically-Active Compound

| | |
|---|---|
| water, sterile and deionized | 49.10% |
| insulin, human recombinant, 28.5 units/mg (Biobras) | 0.87% |
| triethanolamine, NF - pH modifier | 0.03% |

The resulting composition was a stable emulsion in which the dispersed phase consisted of liquid droplets which were uniformly dispersed in the composition and which comprised the enhancer dissolved in the solvents comprising the crystallization inhibitor and the Ostwald-ripening inhibitor. The continuous phase comprised an aqueous solution of propylene glycol, glycerin, preservative, and pharmaceutically-active compound. The pH modifier was associated with the emulsifier. One hundred microliters of the composition contained approximately 25 international units (IU) of human recombinant insulin. The composition had a pH of 7.81.

Example No. 2

This example describes the preparation of a composition which can be used as an intra-nasal spray for the delivery of GHRP-6 (H-His-D-Trp-Ala-Trp-D-Phe-Lys-$NH_2$).
Premix

| | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.67% |
| petrolatum - Protopet (Witco) - solvent, Ostwald-ripening inhibitor | 0.14% |
| Part B | |
| propylene glycol, USP - solvent | 1.00% |
| glycerin, USP - cosolvent, emollient, humectant and protein stabilizer | 2.00% |
| water, sterile and deionized | 44.05% |
| Part C | |
| acrylates/$C_{10-30}$ alkyl acrylate crosspolymer - Pemulen TR2, NF grade (Noveon, Inc.) - emulsifier and thickener | 0.10% |
| Part D | |
| benzalkonium chloride, 50% aqueous solution - Maquat (Mason) - preservative | 0.01% |
| Part E | |
| triethanolamine, NF - pH modifier | 0.03% |

Solution of Pharmaceutically-Active Compound

| | |
|---|---|
| water, sterile and deionized | 49.10% |
| GHRP-6 (Bachem) - pharmaceutically-active compound | 0.87% |
| triethanolamine, NF - pH modifier | 0.03% |

The resulting composition comprised a stable emulsion in which the dispersed phase consisted of liquid droplets which were uniformly dispersed in the composition and which consisted of the enhancer dissolved in the solvents comprising the crystallization inhibitor and the Ostwald-ripening inhibitor. The continuous phase comprised an aqueous solution of propylene glycol, glycerin, preservative, and pharmaceutically-active compound. The pH modifier was considered to be associated with the emulsifier. One hundred microliters of the composition contained approximately 100 micrograms of GHRP-6.

Example No. 3

This example describes the preparation of a composition that can be used as an intra-nasal spray for the delivery of human recombinant insulin. The present composition differs from that described in Example No. 1 in that it contains surfactants to reduce the particle size of the liquid droplets of the emulsion. The use of surfactants results in smaller particle sizes, allowing for a more homogenous distribution of the dispersed phase in the continuous phase and assists in the prevention of Ostwald ripening. The surfactants used in this example are at a level below that which may cause irritation.
Premix

| | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.41% |
| petrolatum - Protopet (Witco) - solvent, Ostwald-ripening inhibitor | 0.28% |
| PEG-20 sorbitan monostearate - Crillet 3 (Croda) - surfactant | 0.20% |
| Part B | |
| propylene glycol, USP - solvent | 1.00% |
| glycerin, USP - cosolvent, emollient, humectant and protein stabilizer | 2.00% |
| PEG-60 corn glycerides - Crovol - 70 (Croda) - surfactant | 0.20% |
| water, sterile and deionized | 43.77% |
| Part C | |
| acrylates/$C_{10-30}$ alkyl acrylate crosspolymer - Pemulen TR2, NF Grade - emulsifier and thickener | 0.10% |
| Part D | |
| benzalkonium chloride, 50% aqueous solution - Maquat (Mason) - preservative | 0.01% |
| Part E | |
| triethanolamine, NF - pH modifier | 0.03% |

Solution of Pharmaceutically-Active Compound

| | |
|---|---|
| water, sterile and deionized | 49.10% |
| insulin, human recombinant, 28.5 unit/mg (Biobras) | 0.87% |
| triethanolamine, NF - pH modifier | 0.03% |

The resulting composition is a stable emulsion in which the dispersed phase consisted of liquid droplets which were dispersed uniformly in the composition and which included the enhancer dissolved in the solvents comprising the crystallization inhibitor and the Ostwald-ripening inhibitor. The continuous phase comprised an aqueous of propylene glycol, glycerin, preservative, and pharmaceutically-active compound. The pH modifier and the surfactant were considered to be associated with the polymeric emulsifier. One hundred microliters of the composition contained approximately 25 IU of human recombinant insulin. The composition had a pH of 7.7.

Example No. 4

This example describes the preparation of a composition which can be used as an intra-nasal spray for the delivery of insulin. The present composition includes Vitamin E acetate solvent used as both a crystallization inhibitor and as a preservative. The present composition differs from that described in Example Nos. 1 and 3 in that a commercial aqueous insulin solution is used. In addition, the present composition demonstrates that the acrylates/$C_{10\text{-}30}$ alkyl acrylate crosspolymer emulsifier is capable of substantially inhibiting Ostwald ripening without the need for a separate Ostwald-ripening inhibitor.

Premix

|  | Wt % |
|---|---|
| Part A | |
| oxacyclohexadecan-2-one (Firmenich) - enhancer | 2.00% |
| Vitamin E acetate, USP (VGF) - solvent, crystallization inhibitor and preservative | 0.25% |
| Part B | |
| glycerin, USP - cosolvent, emollient, humectant and protein stabilizer | 1.00% |
| water - sterile and deionized | 46.59% |
| Part C | |
| acrylates/$C_{10\text{-}30}$ alkyl acrylate crosspolymer - Pemulen TR2, NF Grade (Noveon, Inc.) - emulsifier and thickener | 0.08% |
| Part D | |
| TRIS amino, USP - pH modifier | 0.08% |

The Premix was prepared as follows. The ingredients of Part A were mixed by mechanically stirring at 40° C. until homogeneous. The ingredients of Part B were mixed separately using magnetic stirring at 40° C. until homogeneous and then added to Part A. The resulting mixture was stirred vigorously and Part C was added slowly to the mixture. The mixture was allowed to cool to room temperature while stirring for 18 hours. Part D was then added and the resulting mixture was shaken and stirred for 4 hours.

Fifty grams of the Premix and 50.0 mL of 500 units/mL Humulin® 500 (Lilly) (human recombinant insulin) were mixed and rolled at 120 rpm on a roller mill for one hour. The resulting homogeneous stable emulsion comprised a dispersed phase of liquid droplets in which the enhancer was dissolved in Vitamin E acetate and a continuous phase which comprised an aqueous solution of insulin, glycerin, and water. The pH modifier was considered to be associated with the emulsifier. The dispersed phase was uniformly distributed in the composition.

Example No. 5

This example describes the preparation of a composition which can be used as an intra-nasal spray for the delivery of oxycodone. Oxycodone was used in the form of its free base prepared from the commercially available hydrochloride salt by dissolving in 20 parts of water and a stoichiometric amount of 1.0 N sodium hydroxide. The precipitate was collected and washed with water. The precipitate was then dried at room temperature using a vacuum pump.

Oxycodone Intra-Nasal Preparation

|  | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.67% |
| petrolatum - Protopet (Witco) - solvent, Ostwald-ripening inhibitor | 0.14% |
| oxycodone, free base - pharmaceutically-active compound | 2.00% |
| Part B | |
| acrylates/$C_{10\text{-}30}$ alkyl acrylate crosspolymer - Pemulen TR2, NF Grade (Noveon, Inc.) - emulsifier and thickener | 0.08% |
| Part C | |
| glycerin, USP - cosolvent, emollient, humectant and protein stabilizer | 2.10% |
| water, sterile and deionized | 93.00% |
| benzalkonium chloride, 50% aqueous solution - Maquat (Mason) - preservative | 0.01% |

The ingredients of Part A were combined at 40° C. by mechanical stirring until a paste was formed. Part B was then combined with Part A by mechanically stirring at 40° C. until a homogeneous paste was formed. Part C was then added and the resulting mixture was stirred mechanically at room temperature until a white homogeneous emulsion was formed.

The free base of oxycodone, which is insoluble in water, is strong enough to stabilize emulsions formed using acrylates/$C_{10\text{-}30}$ alkyl acrylate emulsifier. This enables the composition to exist in the form of a cohesive homogeneous emulsion without the need for use of further pH modifiers and in order to avoid the formation of an inorganic salt. The dispersed phase consisted of the enhancer dissolved in the solvents comprising the crystallization inhibitor and the Ostwald-ripening inhibitor. The continuous phase consisted of glycerin, preservative, and water. The pharmaceutically-active compound was considered to be associated with the acrylates/$C_{10\text{-}30}$ alkyl acrylate crosspolymer emulsifier.

One hundred microliters of the composition contained approximately 2 milligrams of oxycodone.

The invention claimed is:

1. A pharmaceutical composition in the form of an emulsion and comprising: (A) a continuous liquid phase; (B) liquid droplets dispersed in said liquid phase; (C) a pharmaceutically-active compound; (D) a Hsieh enhancer; (E) a hydrocolloid emulsifying agent; and (F) a crystallization inhibitor in an amount sufficient to inhibit crystallization of at least one compound in the pharmaceutical composition, wherein the crystallization inhibitor is cottonseed oil.

* * * * *